United States Patent [19]

Burba et al.

[11] Patent Number: 5,175,220

[45] Date of Patent: Dec. 29, 1992

[54] IMIDAZOLYL DERIVATIVES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING SAID IMIDAZOLYL DERIVATIVES

[75] Inventors: Christian Burba, Herbern; Werner Mrotzek, Dortmund, both of Fed. Rep. of Germany

[73] Assignee: Schering AG, Bergkamen, Fed. Rep. of Germany

[21] Appl. No.: 816,566

[22] Filed: Jan. 3, 1992

Related U.S. Application Data

[62] Division of Ser. No. 677,629, Mar. 28, 1991.

[30] Foreign Application Priority Data

Apr. 2, 1990 [DE] Fed. Rep. of Germany ....... 4010548

[51] Int. Cl.$^5$ ................... C07D 233/61; C08G 59/50
[52] U.S. Cl. ................... 525/526; 548/313.7; 548/335.5; 528/94; 528/117; 525/502; 525/504; 525/523; 525/529; 525/531; 428/413; 427/386
[58] Field of Search ............ 548/336, 341; 528/94, 528/117; 525/523, 526, 529, 531, 502, 504; 428/413; 427/386

[56] References Cited

U.S. PATENT DOCUMENTS

| | | | |
|---|---|---|---|
| 3,756,984 | 9/1973 | Klaren et al. ................ | 525/524 |
| 4,066,625 | 1/1978 | Bolger ......................... | 525/523 |
| 4,420,605 | 12/1983 | Kaufman ..................... | 525/504 |

FOREIGN PATENT DOCUMENTS

| | | |
|---|---|---|
| 0212852 | 3/1987 | European Pat. Off. . |
| 1954504 | 6/1970 | Fed. Rep. of Germany . |
| 3033131 | 4/1982 | Fed. Rep. of Germany . |
| 2144724 | 2/1973 | France . |
| 2394593 | 1/1979 | France . |

*Primary Examiner*—Melvyn I. Marquis
*Assistant Examiner*—Frederick Krass
*Attorney, Agent, or Firm*—Curtis, Morris & Safford

[57] ABSTRACT

The invention relates to new compounds of the general formulas

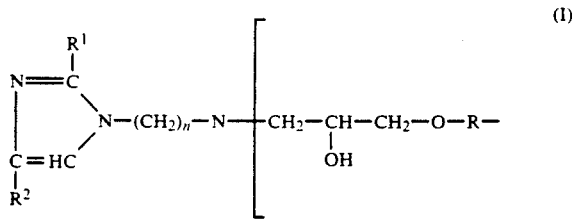

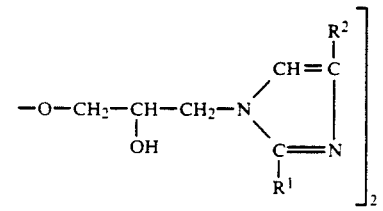

and

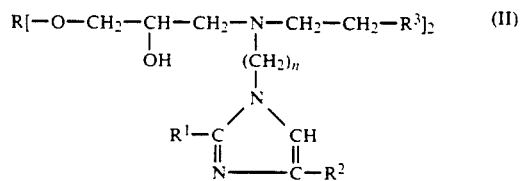

where R is a divalent, optionally branched aliphatic, cyclic or alicyclic hydrocarbon group having from 2 to 10 carbon atoms; $R^1$ and $R^2$ are, independently of one another, hydrogen, or aliphatic or aromatic hydrocarbon groups; $R^3$ is —COOH, —CN, —COOC$_2$H$_4$—OH, —CONH—NH$_2$ or —COOR$^4$; $R^4$ is an aliphatic hydrocarbon group having from 1 to 4 carbon atoms; and n is 2 or 3.

4 Claims, No Drawings

IMIDAZOLYL DERIVATIVES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING SAID IMIDAZOLYL DERIVATIVES

This application is a division of application Ser. No. 07/677,629, filed Mar. 28, 1991.

The invention relates to new imidazolyl derivatives, their use as curing agents in epoxy-resin compositions, and curable epoxy-resin compositions incorporating said imidazolyl derivatives and comprising an epoxy resin and compounds of the general formula (I), and optionally commonly used curing agents and solvents, for the manufacture of molded articles.

In the manufacture of composite materials, two basic principles are employed today.

One of these is the wet lay-up process, a one-step process in which reinforcing materials are impregnated with a curable mixture and heat-cured in one step to the thermoset final state.

In the other process, the two-step process, so-called prepregs are first produced from reinforcing materials and a curable mixture, and these prepregs are then processed into finished parts in a separate second step. With respect to operating procedure, a distinction is made between working with and working without solvents.

The prepregs are normally produced in a continuous operation in which the reinforcing materials are passed through an impregnating bath of the resin/curing agent mixture being used, or the impregnant is mixed only just before it is applied to the base material and then spread thereon with a special device. The amount of impregnant to be applied to a given base-material web is controlled not only through the viscosity of the impregnant but also through squeeze rolls located downstream.

With solvent-containing systems, the solvent contained in the impregnating solution is evaporated through heat input after the impregnating operation, and the resin system is converted at the same time from the A stage to the B stage. Depending on the operating conditions and the resin system used, the reinforcing materials impregnated with liquid to highly viscid impregnant are thus turned into a prepreg that is slightly tacky to almost dry. In this process step it is important that the solvent be completely eliminated from the impregnating mixture and that the latent curing agent needed to cure the prepreg in the second process step not be activated just yet, as this would cause the impregnated reinforcing materials to react completely, which is not desired.

With solvent-free systems, depending on the chemical composition of the resin system the material either also undergoes a short heat treatment after impregnation or the reinforcing materials are lined on both sides with release sheets immediately after impregnation, without any separate heat treatment, and placed into intermediate storage appropriate to the system. During this intermediate storage, either a gradual transition of the resin system to the B stage takes place or the impregnant is fixed on the base materials through physical effects alone and largely without chemical changes.

The prepregs so obtained can be stored and shipped as rolls before they are cut to size, as required for the intended end use, and stacked to the thickness of the finished part. Under the simultaneous action of pressure and heat, the prepreg stack is completely cured to give a high-strength molded part, the still low-molecular-weight, fluid resins being thus converted to the high-molecular-weight C stage of a thermoset.

While in the one-step process long open times and short cure times at low cure temperatures are required, prolonged storage stability of the prepregs is an additional requirement in the two-step process. Storage temperatures lower than room temperature have become steadily less acceptable in practice.

Of importance is further that, depending on the prepreg manufacturing method, the viscosity of the ready-to-use curable mixture remains substantially constant for as long a period as possible. This is necessary, especially when an impregnating bath of large volume is used, for achieving constant resin deposition and an invariant B stage since the manufacturing conditions cannot be continually adjusted to changing relationships within the curable mixture and since fluctuations in the viscosity would have an adverse effect on the physical properties of the fully cured end product.

What is desired in practice is a curable mixture whose viscosity remains constant in the impregnating bath for an extended period of time and which can then be stored as a prepreg at room temperature for a long time without undergoing chemical changes.

Regardless of how they are manufactured, the prepregs should cure completely within a short time at the lowest possible temperature, the maximum temperature of the exothermic reaction should remain at a low level even with moderately thick layers, and the profile of physical properties of the finished products should meet practical requirements.

These requirements concerning curing behavior and profile of properties apply also to epoxy-resin systems to be processed by the wet lay-up method.

For certain applications, all that is required and, in fact, desired is a partial cure to the point where the molded articles are dimensionally stable, complete curing taking place, optionally after intermediate storage, in a subsequent tempering operation at the necessary temperatures. However, it is important that even during the partial cure, the thermal stability of the material increase to a level above the cure temperature or otherwise the temperature of the molded article will have to be lowered before it can be removed from the mold.

Dicyandiamide, long used as a latent curing agent in curable mixtures based on epoxy resins, is usually combined with co-curing agents and/or accelerators to obtain the desired properties. A great many suggestions for its use in this field are known from the literature.

While dicyandiamide solutions can be used to produce homogeneous substrates, the use of solvents gives rise to other problems.

Dicyandiamide is soluble in sufficient amounts in only a few solvents, particularly dimethylformamide and methyl glycol. However, these solvents are toxicologically hazardous and create problems both in the manufacture of the prepregs, that is, during impregnation of the reinforcing materials and conversion to the B stage, and in waste disposal.

Since dicyandiamide is only sparingly soluble, rather large amounts of solvents must be used, and these affect the impregnating viscosity in such a way that the binder content on the reinforcing materials cannot be chosen as desired.

Since these solvents cannot be removed completely during the cure, there is, moreover, the danger that when the finished parts are subjected to thermal stresses the material will fail prematurely and/or the solvents will be given off uncontrolled to the ambient air in the field.

When solid crystalline dicyandiamide is used without solvents in liquid epoxy resins, the necessary amount of dicyandiamide is either dispersed directly in the epoxy resin or a highly filled dicyandiamide/epoxy resin paste is first prepared and later adjusted with the bulk of the epoxy resin to the desired resin/curing agent concentration.

In either case, preparation of the dispersions is not a simple matter. Moreover, when standing for an extended period of time, particularly under impregnating conditions, the dispersions tend to separate.

When solid crystalline dicyandiamide is used without solvents in epoxy resins which at room temperature are solid, a paste of dicyandiamide and liquid epoxy resins is also first prepared and then worked into the solid-resin melt at elevated temperature.

Apart from the problems outlined, undesired amounts of liquid epoxy resins are introduced into the solid resin when this operating procedure is employed.

Moreover, when solid crystalline dicyandiamide is used, inhomogeneities which are due to undissolved and unreacted particles are observed in the cured substrates.

The present invention seeks to overcome the drawbacks of the prior art and to provide curable mixtures, based on epoxy compounds and latent curing agents soluble or homogeneously dispersible in the epoxy resins, which partially cure to the dimensionally stable state or completely cure to the thermoset final state at relatively low temperatures within a short time and without high peak exotherms, whose thermal stability meets practical requirements, and in which prepregs have adequate storage stability at room temperature.

This goal is attained through the use of a new curing agent, optionally with the concurrent use of conventional latent curing agents.

The invention thus, in one respect, relates to compounds of the general formulas

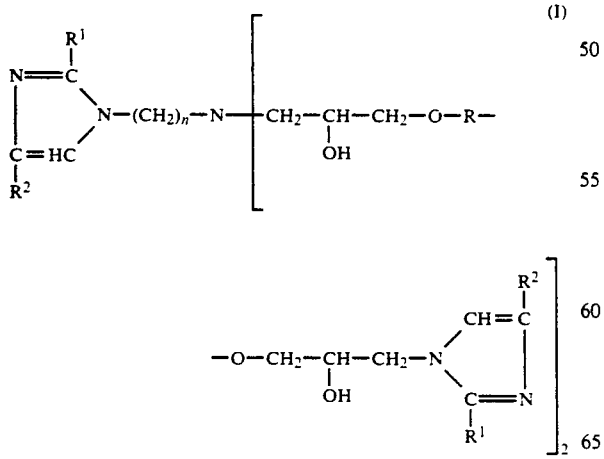

and

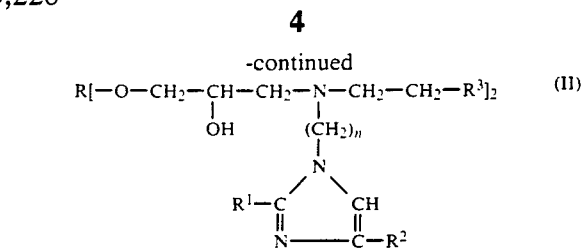

where R is a divalent, optionally branched aliphatic, cyclic or alicyclic hydrocarbon group having from 2 to 10, and more particularly from 4 to 8, carbon atoms; $R^1$ and $R^2$ are, independently of one another, hydrogen, or aliphatic or aromatic hydrocarbon groups, and more particularly H, $CH_3$ or $C_2H_5$; $R^3$ is —COOH, —CN, —COOC$_2$H$_4$—OH, —CONH—NH$_2$ or —COOR$^4$; $R^4$ is an aliphatic hydrocarbon group having from 1 to 4 carbon atoms, and more particularly —CH$_2$—CH$_2$—OH; and n is 2 or 3.

The invention further relates to curing agents for glycidyl compounds which can be prepared by reacting (A) imidazolyl compounds of the general formula

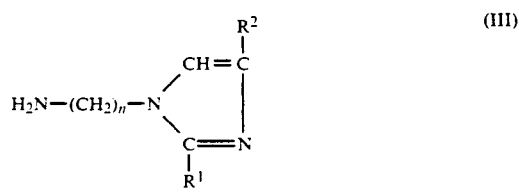

where $R^1$ and $R^2$ are, independently of one another, aliphatic or aromatic hydrocarbon groups, and more particularly H, $CH_3$ or $C_2H_5$, and n is 2 or preferably 3, with (B) glycidyl ethers of the general formula

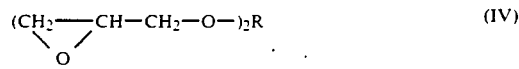

where R is a divalent, optionally branched aliphatic, cyclic or alicyclic hydrocarbon group having from 2 to 10, and more particularly from 4 to 8, carbon atoms, in a molar ratio of (A) to (B) of from 1:2 to 2:1, and optionally further reacting these addition compounds with (C) (1) acrylic acid or derivatives of acrylic acid of the general formula

where $R^3$ is —COOH, —CN, —CONH—NH$_2$, —COOH$_2$H$_4$OH or —COOR$^4$ and $R^4$ is an aliphatic hydrocarbon group having from 1 to 4 carbon atoms when the addition product of (A) and (B) contains amine hydrogen atoms, or with (2) imidazoles of the general formula

where $R^1$ and $R^2$ are, independently of one another, H, $CH_3$, $C_2H_5$ or phenyl when the addition product of (A) and (B) contains free epoxy groups, the compounds of step (C) being used in such amounts that all reactive amine hydrogen atoms or epoxy groups of the addition compounds from (A) and (B) are reacted.

One object of the invention is the use of compounds of the general formulas

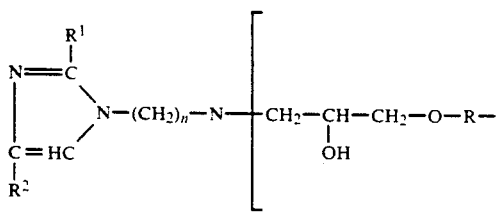
(I)

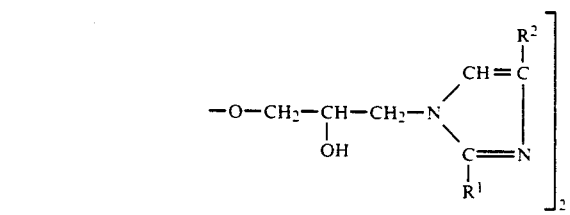

and/or

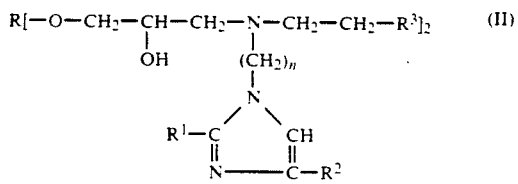
(II)

where R is a divalent, optionally branched aliphatic, cyclic or alicyclic hydrocarbon group having from 2 to 10, and more particularly from 4 to 8, carbon atoms; $R^1$ and $R^2$ are, independently of one another, hydrogen, or aliphatic or aromatic hydrocarbon groups, and more particularly H, $CH_3$ or $C_2H_5$; $R_3$ is —COOH, —CN, —COOC$_2$H$_4$—OH, —CONH—NH$_2$ and —COOR$^4$; $R^4$ is an aliphatic hydrocarbon group having from 1 to 4 carbon atoms, and more particularly —CH$_2$—CH$_2$—OH; and n is 2 or 3, optionally with the concurrent use of commonly used nitrogen-containing heterocyclic amino compounds as curing agents for epoxy resins.

The invention has a further object molded epoxy-resin articles characterized in that in a first step the reinforcements or embedments are impregnated at room temperature with a binder, composed of (a) at least one epoxy resin with more than one epoxy group per molecule on the average;

(b) compounds of the general formulas

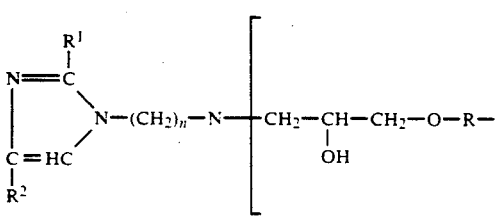
(I)

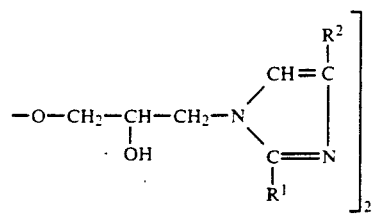

and/or

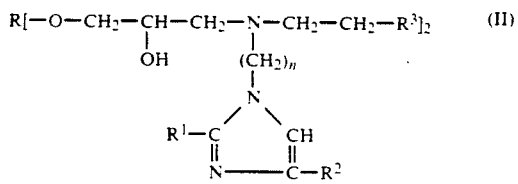
(II)

where R is a divalent, optionally branched aliphatic, cyclic or alicyclic hydrocarbon group having from 2 to 10, and more particularly from 4 to 8, carbon atoms; $R^1$ and $R^2$ are, independently of one another, hydrogen, or aliphatic or aromatic hydrocarbon groups, and more particularly H, $CH_3$ or $C_2H_5$; $R^3$ is —COOH, —CN, —COOC$_2$H$_4$—OH, —CONH—NH$_2$ and —COOR$^4$; $R^4$ is an aliphatic hydrocarbon group having from 1 to 4 carbon atoms, and more particularly —CH$_2$—CH$_2$—OH; and n is 2 or 3; and optionally (c) commonly used solvents, fillers, reinforcements or embedments, pigments and auxiliaries; and optionally (d) commonly used nitrogen-containing heterocyclic amino compounds, and in a first step converted to the solid and dimensionally stable state and then, in a second step, fully cured at a temperature that is below the softening point of the molded articles formed in the first step.

Further objects of the invention are set forth in the claims.

The imidazolyl compounds of the invention can be prepared by addition reactions, the glycidyl ethers being reacted in a first step with N-aminoalkylimidazolyl compounds containing primary amino groups, in a ratio of mols of epoxy compound to mols of primary amino groups that may range from 1:2 to 2:1, and, in a second step, acrylic acid or derivatives of acrylic acid being added to the secondary amino groups formed, and imidazolyl compounds of formula (VI) to the free epoxy groups. The addition reactions of the first and second steps generally are carried out by known procedures.

The glycidyl ethers which, in accordance with the invention, are used to make the addition compounds are products of the reaction of polyhydric alcohols and epichlorohydrin to give chlorohydrin ethers followed by ring formation with alkali-metal hydroxides. These reactions generally are carried out by known methods.

The alcohols here used may be straight- or branched-chain polyhydric aliphatic alcohols, and particularly diols such as butanediol, hexanediol, octanediol, neopentyl glycol or decanediol, or cyclic or alicyclic diols such as 1,4-cyclohexanediol or 1,4-dihydroxymethylcyclohexane.

The imidazolyl compounds which, in accordance with the invention, are used in making the addition products are compounds of the general formula

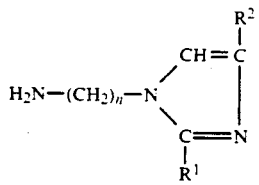  (III)

where $R^1$ and $R^2$ are, independently of one another, aliphatic or aromatic hydrocarbon groups, and more particularly H, $CH_3$ or $C_2H_5$, and n is 2 or preferably 3. From 1 to 2 mols of the imidazolyl compound of formula (III) are used per mol of epoxy compound of the aforesaid glycidyl compounds of formula (IV).

The acrylic acid or derivatives of acrylic acid used in accordance with the invention are compounds of the general formula

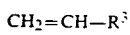  (V)

where $R^3$ is —COOH, —CN, —$COOC_2H_4$—OH, —CONH—$NH_2$ or —$COOR^4$; and $R^4$ is an aliphatic hydrocarbon group having from 1 to 4 carbon atoms, and more particularly $CH_3$ or $C_2H_5$.

One mol of the acrylic acid compounds is used per secondary amino group of the addition compounds made in the first step.

The imidazolyl compounds containing only one amine hydrogen atom which, in accordance with the invention, are added to the addition compounds with free epoxy groups made in a first step are compounds of the general formula

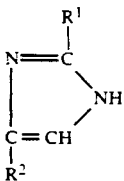  (VI)

where $R^1$ and $R^2$ are, independently of one another, H, $CH_3$, $C_2H_5$ or phenyl. One mol of the compounds of formula (VI) is used per epoxy group.

The addition products which in accordance with the invention can be prepared by these process steps are compounds of the general formulas

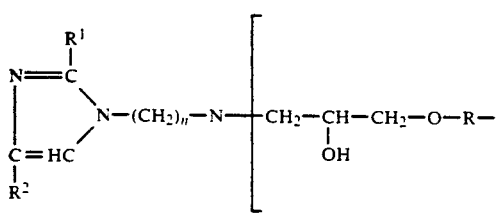  (I)

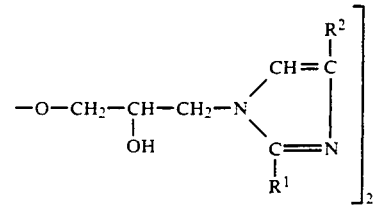

and

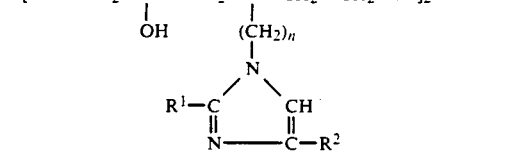  (II)

where R is a divalent, optionally branched aliphatic, cyclic or alicyclic hydrocarbon group having from 2 to 10, and more particularly from 4 to 8, carbon atoms; $R^1$ and $R^2$ are, independently of one another, hydrogen, or aliphatic or aromatic hydrocarbon groups, and more particularly H, $CH_3$ or $C_2H_5$; $R^3$ is —COOH, —CN, —$COOC_2H_4$—OH, —CONH—$NH_2$ or —$COOR^4$; $R^4$ is an aliphatic hydrocarbon group having from 1 to 4 carbon atoms, and more particularly —$CH_2$—$CH_2$—OH; and n is 2 or 3.

Apart from the preferred compounds of the general formulas (I) and (II), which are formed when the ratio between the imidazolyl compounds of formula (III) and the glycidyl compounds of formula (IV) is an even-numbered 1:2 or 2:1, molar ratios between these values will yield structured products which contain the structural unit $$\begin{array}{c} +N-CH_2-CH-CH_2-O-R-O-CH_2-CH-CH \\ | \qquad\qquad | \qquad\qquad\qquad\qquad\qquad | \\ (CH_2)_n \qquad OH \qquad\qquad\qquad\qquad OH \\ | \\ N \\ R^1-C \diagup \diagdown CH \\ \| \qquad\quad \| \\ N———C-R^2 \end{array}$$  (VII)

repeatedly (m) in the chain and have derivatives of either formula (V) or formula (VI) as end groups.

Both m, which is preferably between 1 and 5, and more particularly between 1 and 3, and the end groups can be determined at will through the choice of the molar ratios of compounds of formula (III) to compounds of formula (IV).

It thus becomes possible to control the catalytic activity (tertiary or total nitrogen content) and to adjust the viscosity from low-viscosity to high-viscosity to solid.

It is preferable that the addition products from imidazolyl compounds of formula (III) and glycidyl ethers of formula (IV) be prepared in a first step and either the derivatives of acrylic acid of formula (V) or the imidazoles of formula (VI) be added in a second step.

However, all components may also be reacted simultaneously. A statistical mixture is then obtained which usually is less homogeneous than is the case when a stepwise procedure is employed. So far as its suitability for the end uses contemplated by the invention is concerned, however, no significant difference has been observed.

The curing agents of the invention can be used singly or as a mixture at the rate of from 2 to 35 g, and more particularly from 4 to 25 g, but preferably from 5 to 20 g, of curing agent per 100 g of epoxy resin.

The imidazolyl compounds of the invention can also be used in the form of their salts. Use may here be made of the organic and inorganic salt formers known in this field. In accordance with the invention, however, the mono- or polybasic organic carboxylic acids are preferred, the branched-chain monocarboxylic acids having up to 10 carbon atoms, such as 2-ethylhexoic acid, being particularly well suited.

The epoxy resins which, in accordance with the invention, are used as a binder constituent are glycidyl esters and ethers with two or more epoxy groups per molecule, and preferably the glycidyl ethers based on mono- or polyhydric phenols. In accordance with the invention, glycidyl ethers of 2,2-bis(4-hydroxyphenyl)-propane (bisphenol A) with epoxy values of from 0.2 to 0.6, and particularly the compounds with epoxy values of from 0.45 to 0.55 which are liquid at room temperature, are preferred. The glycidyl ethers based on bisphenol F and the novolacs have also proved advantageous.

Also usable are the commercial halogenated, and more particularly brominated, epoxy resins based on the aforesaid phenols.

The amino compounds which, in accordance with the invention, may also be used are preferably commonly used nitrogen-containing heterocyclic amino compounds, that is, N-alkylimidazoles such as N-methyl- or N-ethylimidazole, and/or imidazoline compounds of the genera formula

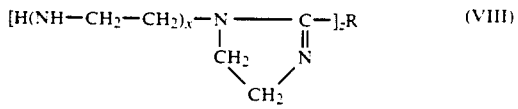

(VIII)

where R is an optionally branched alkyl or alkylene group having fewer than 10 carbon atoms, and more particularly —CH$_3$, —CHOH—CH$_3$ or —(CHR')y, R' is H or CH$_3$, x is 1, 2 or 3, y is from 4 to 8, and z is equal to the valence of R, and particularly those where x is 1, z is 1, and R is —CH$_3$ or —CH$_2$—CH$_3$. Other curing agents commonly used in this field may also be used, if desired.

For modification of the properties of the end product, other epoxy resins may be used concurrently, as may modifiers or auxiliaries such as phenolic resins, melamine resins, silicone resins, inorganic and organic fillers such as quartz powders, titanium dioxide, carbon black, and silicone or butadiene rubber.

To obtain the desired viscosity, resins of different viscosities, diluents, or such commonly used solvents as dimethyl formamide, acetone, methyl ethyl ketone, methyl glycol or propylene glycol monomethyl ether or mixtures thereof may be used.

In prepregging, organic and inorganic fibers, nonwovens and woven fabrics based on aramid, carbon or cellulose, metals such as boron, steel, etc., ceramics and especially glass are used.

The solvent-containing prepregs are generally made by known methods, in which the base materials are impregnated with the reactive resin mixture in an impregnating bath and, after the excess resin has been squeezed off, continuously converted from the A stage to the B stage with input of energy (mostly heat) and simultaneous removal of the solvent. Depending on the desired prepreg consistency (viscid to solid), the prepregs are then provided on both sides with a release sheet and wound into a roll for storage and shipping. The further processing involves cutting the individual prepreg layers to size and assembling them into a stack, from which a highly crosslinked part is produced by shaping with simultaneous heat input.

The curing agents of the invention can also be used successfully in solventless prepregs based on epoxy resins and, optionally, commonly used curing agents. Here the base materials are impregnated at optionally elevated temperature and by conventional methods with the binder system and placed into storage appropriate to the system before they are processed further like the solvent-containing systems.

Further examples of solventless systems are wet layup laminates, base materials for the electrical industry, fiber-reinforced molded parts produced in situ, heat-curing one-component adhesives for the bonding of body sections in the automotive industry (flange-joint adhesives), for example, as well as epoxy-resin castings, epoxy-resin coatings and epoxy-resin filament- or tape-wound structures.

EXAMPLES (I) Preparation of the Curing Agents of the Invention

Example 1

(a) 250 g (2 mols) of 1-(3-aminopropyl)imidazole is introduced as initial charge under nitrogen, preheated to about 70° C., and slowly mixed with 316 g of the diglycidyl ether of hexanediol (epoxy value 0.63). After the exothermic reaction has subsided, stirring is continued for 2 hr at 70° C.

(b) To the adduct produced under (a), 232 g (2 mols) of 2-hydroxyethyl acrylate is added at about 50° C. and stirring is continued for about 2½ hr at 60° C.

| Characteristics: | Amine value: | 263 |
|---|---|---|
| | Viscosity at 60° C.: | 6.2 Pa.s |

Example 2

Salt of polyaddition product of Example 1 (b)

73.5 g of the polyaddition product from 1 (b) is homogeneously mixed with 26.5 g of 2-ethylhexoic acid.

| Characteristics: | Amine value: | 192 |
|---|---|---|
| | Viscosity at 60° C.: | 3.45 Pa.s |

Example 3

The procedure described in Example 1 (a) is followed, except that in place of the diglycidyl ether of hexanediol 274 g of the diglycidyl ether of butanediol (epoxy value 0.73) is used.

| Characteristics: | Amine value: | 271-273 |
|---|---|---|
| | Viscosity at 60° C.: | 12.7 Pa.s |

Example 4

The procedure described in Example 1 (a) and (b) is followed, except that in place of the diglycidyl ether of hexanediol 308 g of the diglycidyl ether of neopentyl (epoxy value 0.65) is used.

| Characteristics: | Amine value: | 264–268 |
|---|---|---|
| | Viscosity at 60° C.: | 9.35 Pa.s |

Example 5

The procedure described in Example 1 (a) and (b) is followed, except that in place of the diglycidyl ether of hexanediol 345 g of the diglycidyl ether of cyclohexanedimethylol (epoxy value 0.58) is used.

| Characteristics: | Amine value: | 289–291 |
|---|---|---|
| | Viscosity at 60° C.: | 22.8 Pa.s |

Example 6

62.5 g (0.5 mol) of 1-(3-aminopropyl)imidazole and 82.0 g (1.0 mol) of 2-methylimidazole are introduced as initial charge under nitrogen in 100 g of ethanol, heated to about 60° C.–70° C., and slowly mixed with 316 g (1 mol) of the diglycidyl ether of hexanediol with stirring. After the reaction has subsided, stirring is continued for 1 hr at 70° C. After the ethanol has been drawn off, a product is obtained which has the following characteristics:

Amine value: 239
Viscosity at 60° C.: 50 Pa.s

Example 7

125 g (1 mol) of 1-(3-aminopropyl)imidazole is introduced as initial charge at 60° C. and slowly mixed with 158 g (0.5 mol) of the diglycidyl ether of hexanediol. After the exothermic reaction has subsided, the mixture is allowed to react for another hour at about 70° C., then cooled to 50° C., slowly mixed with 53.0 g (1 mol) of acrylonitrile, and reacted for another 2 hr at 60° C.

| Characteristics: | Amine value: | 325 |
|---|---|---|
| | Viscosity at 25° C.: | 80 Pa.s |

Example 8

187.5 g (1.5 mols) of 1-(3-aminopropyl)imidazole is introduced as initial charge and slowly mixed at 60° C. with 316 g (1 mol) of the diglycidyl ether of hexanediol. After the exothermic reaction has subsided, the mixture is allowed to react for another hour at 70° C. and then mixed with 116 g (1 mol) of hydroxyethyl acrylate and reacted for another 2 hr at 70° C.

| Characteristics: | Amine value: | 230 |
|---|---|---|
| | Viscosity at 25° C.: | 85 Pa.s |

(II) Preparation of a Prepreg Reaction Mixture

Example 1

100 g of an epoxy resin (epoxide equivalent weight about 190) is mixed with 14 g of the inventive reaction product of (I) 1 and used to make prepregs. This mixture has a viscosity at room temperature (25° C.) of 15.0 Pa.s and is workable even after 10 hours.

The prepregs are produced on the laboratory scale by spreading the reaction mixture onto a glass-filament fabric in a satin weave, measuring about 0.1 m², which after impregnation is lined on both sides with release sheets and then stored at room temperature.

After 24-hour storage at room temperature, the material has aged sufficiently to be processed as a slightly tacky prepreg in several layers by the hot-press molding method at 0.1 bar and temperatures of from 100° C. to 120° C., in from 30 minutes to 1 hour, into high-strength molded articles. The finished product, fully cured in this manner, exhibits no flaws of any kind with respect to adhesion of the individual prepreg layers.

The storage-stability values given in Table 1 are determined on the basis of conditions duplicating those used in actual practice. The impregnated fabric is stored between two polyethylene sheets at 23° C. under standard climatic conditions. A layer of a specimen is molded at 24-hour intervals under conditions duplicating those used in actual practice (1 hr, 120° C.,0.1 bar). The storage-stability value indicated is based on the last day on which the resin is fluid under hot-press molding conditions. The other storage-stability values given in Table 1 are determined in the same way as the one for Example 1.

TABLE 1

Storage stability of solventless prepregs

| Example | Curing agent, Example | Curing agent, g | Epoxy resin, 100 g | Storage stability, days |
|---|---|---|---|---|
| 1 | (I) 1 | 14 | Bisphenol A type, epoxy value 0.53 | >40 |
| 2 | (I) 1 | 14 | Bisphenol A type, epoxy value 0.53 | >20 |
| 3 | (I) 1 | 14 | Bisphenol A type, epoxy value 0.53 | >20 |
| 4 | (I) 2 | 14 | Bisphenol A type, epoxy value 0.53 | >10 |
| 5 | (I) 2 | 14 | Bisphenol A type, epoxy value 0.53 | >10 |
| 6 | (I) 2 | 14 | Bisphenol A type, epoxy value 0.53 | >10 |
| 7 | (I) 3 | 14 | Bisphenol A type, epoxy value 0.53 | About 3 |
| 8 | (I) 4 | 14 | Bisphenol A type, epoxy value 0.53 | >10 |

(III) Determination of Influence of Curing Agent

To determine the properties of the curing agent as a function of structure, the mixtures, composed only of epoxy resin and curing agent so as to eliminate any distorting influences of reinforcements and additives, are fully cured and tested.

In the examples listed in Table 2, a glycidyl ether based on bisphenol A and having an epoxy value of 0.53 is used as epoxy resin.

To produce the test specimens, 100 g of epoxy resin is mixed in each case at room temperature with 14 g of curing agent and cured in a steel mold for 2 hours at 120° C. to give flat molded parts 4 mm thick. From these molded parts, test specimens are then taken by sawing or milling. On these test specimens, the properties specified in Table 2 are determined in conformity with the test standards listed below.

|  |  | Test-specimen dimensions |
|---|---|---|
| Flexural strength | DIN 53.452 | 80 × 10 × 4 mm |
| Deflection | DIN 53.452 | 80 × 10 × 4 mm |
| Impact Strength | DIN 53.454 | 50 × 6 × 4 mm |
| Tentile strength | DIN 53.455 | Dumbbell No. 3 |
| Elongation | DIN 53.455 | Dumbbell No. 3 |
| Modulus of elasticity | DIN 53.457 | Dumbbell No. 3 |
| Heat-distortion temperature | DIN 53.461 | 120 × 10 × 4 mm |
| Glass-transition temperature | DIN 53.445 | 80 × 10 × 1 mm |

TABLE 2

Thermal and mechanical properties

| Example (unit) | 1 | 2 | 3 | 4 |
|---|---|---|---|---|
| Flexural strength (N/mm²) | 91 | 59 | 53 | 53 |
| Deflection (mm) | 7.9 | 6.2 | 5.1 | 5.3 |
| Impact strength (kj/m²) | 14.6 | 7.0 | 2.3 | 2.6 |
| Tensile strength (N/mm²) | 64 | 49 | 57 | 70 |
| Elongation (%) | 3.8 | 2.4 | 2.6 | 4.6 |
| Modulus of elasticity (N/mm²) | 2430 | 2670 | 2950 | 2850 |
| Heat-distortion temperature (°C.) | 122 | 115 | 128 | 128 |
| Glass-transition temperature (°C.) | 149 | 131 | 161 | 156 |
| Example | 5 | 6 | 7 | 8 |
| Flexural strength | 47 | 71 | 60 | 66 |
| Deflection | 4.6 | 7.6 | 6.4 | 7.0 |
| Impact strength | 2.5 | 6.0 | 3.0 | 3.8 |
| Tensile strength | 64 | 40 | 60 | 53 |
| Elongation | 3.4 | 1.7 | 2.9 | 2.4 |
| Modulus of elasticity | 2770 | 2820 | 2960 | 2790 |
| Heat-distortion temperature | 128 | 128 | 133 | 123 |
| Glass-transition temperature | 159 | 162 | 160 | 151 |

We claim:

1. A compound of the general formula

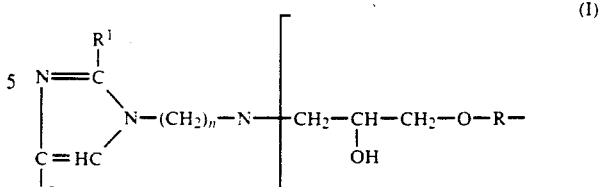

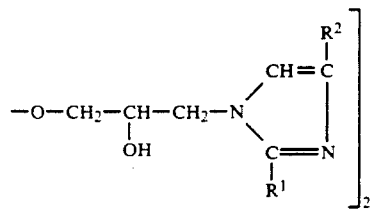

where R is a divalent, optionally branched aliphatic, cyclic or alicyclic hydrocarbon group having from 2 to 10 carbon atoms; $R^1$ and $R^2$ are, independently of one another, hydrogen, or an aliphatic or aromatic hydrocarbon group; and n is 2 or 3.

2. A compound of the general formula

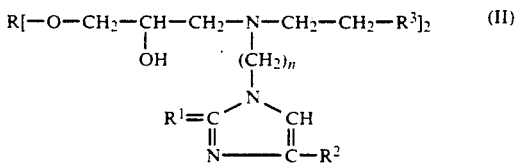

where R is a divalent, optionally branched aliphatic, cyclic or alicyclic hydrocarbon group having from 2 to 10 carbon atoms; $R^1$ and $R^2$ are, independently of one another, hydrogen, or an aliphatic or aromatic hydrocarbon group; $R^3$ is —COOH, —CN, —COOC$_2$H$_4$—OH, —CONH—NH$_2$ or —COOR$^4$; $R^4$ is an aliphatic hydrocarbon group having from 1 to 4 carbon atoms, and n is 2 or 3.

3. A method for preparing a curing agent for glycidyl compounds which comprises reacting (A) an imidazolyl compound of the general formula

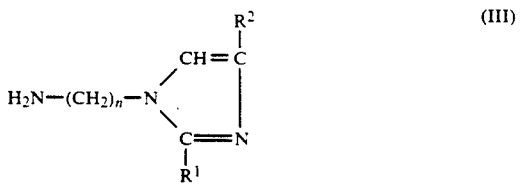

where $R^1$ and $R^2$ are, independently of one another, hydrogen, or an aliphatic or aromatic hydrocarbon group, and n is 2 or 3, with (B) a glycidyl ether of the general formula

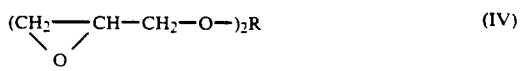

where R is a divalent, optionally branched aliphatic, cyclic or alicyclic hydrocarbon group having from 2 to 10 carbon atoms, in a molar ratio of (A) to (B) of from 1:2 to 2:1.

4. The method for preparing a curing agent for glycidyl compounds as claimed in claim 3, which further comprises reacting an addition product formed from the reaction of (A) and (B) when the addition product of (A) and (B) contains amine hydrogen atoms, with
(C) (1) acrylic acid or a derivative of acrylic acid of the general formula $$CH_2=CH-R^3 \qquad (V)$$

where $R^3$ is $-COOH$, $-CN$, $-CONH-NH_2$, $-COOC_2H_4-OH$ or $-COOR^4$; $R^4$ is an aliphatic hydrocarbon group having from 1 to 4 carbon atoms, or when the addition product of (A) and (B) contains free epoxy groups, with
(2) an imidazole of the general formula

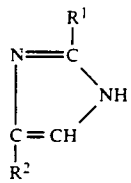
(VI)

where $R^1$ and $R^2$ are, independently of one another, H, $CH_3$, $C_2H_5$ or phenyl,
the compound (C) being used in such amounts that all reactive amine hydrogen atoms or epoxy groups of the addition produce of (A) and (B) are reacted with the compound (C).

* * * * *